United States Patent [19]
Valentine et al.

[11] Patent Number: 5,320,847
[45] Date of Patent: Jun. 14, 1994

[54] AGGLOMERATED PSYLLIUM HYDROPHILIC MUCILLOID COMBINATES

[75] Inventors: William Valentine; William K. Valentine, both of Lawrenceville, Ga.

[73] Assignee: Valentine Enterprises, Inc.

[21] Appl. No.: 61,200

[22] Filed: May 13, 1993

[51] Int. Cl.⁵ ............... A61K 9/16; A61K 31/725; A61K 35/78
[52] U.S. Cl. .................... 424/439; 424/195.1; 424/489; 424/496; 514/782; 514/892; 514/974; 514/911
[58] Field of Search ........... 424/439, 489, 496, 195.1; 514/782, 892, 974, 911

[56] References Cited

U.S. PATENT DOCUMENTS

| | | | |
|---|---|---|---|
| 4,459,280 | 7/1984 | Colliopoulos et al. | 424/35 |
| 4,548,806 | 10/1985 | Colliopoulos et al. | 424/35 |
| 4,851,392 | 7/1989 | Shaw et al. | 424/441 |
| 4,911,917 | 3/1990 | Kuhrts | 424/10 |
| 4,965,252 | 10/1990 | Kuhrts | 514/54 |
| 5,023,245 | 6/1991 | Kuhrts | 514/54 |
| 5,073,370 | 12/1991 | Meer et al. | 514/892 |
| 5,096,714 | 3/1992 | Kuhrts | 424/439 |
| 5,149,541 | 9/1992 | Leis, Jr. et al. | 424/493 |

FOREIGN PATENT DOCUMENTS 2030448  5/1991  Canada.

*Primary Examiner*—Thurman K. Page
*Assistant Examiner*—James M. Spear
*Attorney, Agent, or Firm*—DeLio & Peterson

[57] ABSTRACT

A high-fiber, consumable bulk fiber composition, which may be used as a laxative, comprises powdered psyllium husks agglomerated with a water soluble, low viscosity gum, preferably gum acacia, to form a dry, free-flowing, water dispersible dietary fiber combinate. To form the dietary fiber combinate, the powdered psyllium husks are mixed with an aqueous solution of the water soluble, low viscosity gum, preferably by fluid bed agglomeration, and dried. The composition is employed to treat constipation by ingesting an effective amount of the dietary fiber combinate dispersed in water.

18 Claims, No Drawings

AGGLOMERATED PSYLLIUM HYDROPHILIC MUCILLOID COMBINATES

BACKGROUND OF THE INVENTION

1. Field of the Invention

This invention relates to a method of agglomerating, and thereby increasing the dispersability and mixability of, a powdered psyllium hydrophilic mucilloid combinate by applying an aqueous agglomerating solution containing a soluble, naturally occurring, low viscosity, nutritional fiber. The method of agglomerating powdered psyllium mucilloid in such a manner keeps the total dietary fiber at a maximum while imparting attributes of dispersability and mixability to the final product when added to water. The process aspect of the invention relates to a novel agglomeration process utilizing acacia dissolved in water as the agglomerating agent.

2. Background Art

Psyllium hydrophilic mucilloid consists of the mucillagenous husk portion of blond psyllium seed husks used a as fine powder. Psyllium hydrophilic mucilloid demonstrates a rapidly gelling character when dispersed in water. Because of its gel forming properties, it has been proven useful not only in the case of laxation to relieve constipation but also in the broader use as an internal regulator of the gastro-intestinal system. The main physiological use for ingested psyllium hydrophilic mucilloid, dispersed in water, is as an intestinal bulking agent for defecation regularity assurance. However, it is noted that psyllium ingested as a hydrated mucilloid does not increase intestinal transit time, but rather assures adequate stool bulking principally by increasing the stool bio-mass. Presently available commercial products containing hydrophilic psyllium mucilloid are either comprised of large particles or are difficult to disperse in a lump free fashion; in any event either aspect creates a final product that is less than desirable. In addition, the taste of the psyllium hydrophilic mucilloid dispersed in water, at approximately 3.5g per 8 ounces of water, is found to be objectionable to many users.

One approach to alleviate the problems associated with the water dispersion of psyllium hydrophilic mucilloid is to blend it with 50 percent by weight of a soluble sugar such as dextrose or sucrose. There is some degree of improvement in dispersability and taste but the caloric content increases dramatically. The presence of large concentrations of simple sugars renders the product unusable, for example, to diabetics. The concept of diluting or admixing the psyllium hydrophilic mucilloid is widely known and commercially practiced, as referenced by Goodman and Gilman, *The Pharmacological Basis of Therapeutics*, 4th Ed., p. 1026. U.S. Pat. No. 3,455,714 describes a method for improving the dispersability in water by the use of synthetic cellulose derivatives.

U.S. Pat. No. 4,321,263 describes another approach by a method of increasing the water dispersability of psyllium hydrophilic mucilloid by granulating or agglomerating the psyllium with an alcoholic solution of polyethylene glycol and/or polyvinylpyrrolidone. Yet another approach is disclosed in U.S. Pat. No. 4,548,806 by a method for coating psyllium hydrophilic mucilloid with from about 3-11 percent by weight of a water soluble maltodextrin. However, the presence of the maltodextrin reduces the fiber content of the composition and the dosage must be increased accordingly. Furthermore, the dispersability and mixability of these forms of the psyllium husk powder leaves much to be desired to effect most efficient ingestion when mixed with water.

It would be desirable to eliminate a free sugar as the dispersing agent for the psyllium hydrophilic mucilloid so as to produce a composition that may be used by diabetics and others whose sugar intake is restricted. Any such composition should be able to employ a suitable low calorie, high intensity sweetening agent or blend of sweetening agents. Additionally, it is also desirable that the composition be adapted to carry a variety of additional nutritional agents such as beta carotene, vitamin E, and/or sennosides along with the high intensity sweeteners when combined with a fine powder psyllium mucilloid.

It is therefore an object of the present invention to facilitate a water dispersible psyllium hydrophilic mucilloid composition that is natural in composition and does not substantially reduce the total fiber content of the combinate.

It is another object of the present invention to facilitate a water dispersible psyllium hydrophilic mucilloid composition that has an acceptable level of a high intensity sweetening agent without substantial sacrifice or compromise of the fiber content of the combinate.

It is another object of the present invention to facilitate a combinate of water dispersible psyllium hydrophilic mucilloid with sennoside concentrates and high intensity sweeteners to effect an acceptable overnight laxative composition.

It is yet another object of the present invention to agglomerate psyllium hydrophilic mucilloid powder and high intensity sweeteners and natural flavors in such a manner as to effect a pleasant tasting water dispersible combinate.

It is still another object of the present invention to agglomerate psyllium hydrophilic mucilloid fine powder, high intensity sweeteners, natural flavors and effective amounts of nutritional additives such as beta carotene or vitamin E, or additional laxatives such as sennoside concentrates, in such a manner as to effect a pleasant tasting, water dispersible combinate.

SUMMARY OF THE INVENTION

The above and other objects, which will be apparent to those skilled in the art, are accomplished in the present invention in which it has been discovered that a high-fiber, consumable bulk fiber composition, which may also be employed as a laxative, comprises powdered psyllium husks agglomerated with a water soluble, low viscosity gum, preferably gum acacia, to form a dry, free-flowing, water dispersible dietary fiber combinate. To form the dietary fiber combinate, the powdered psyllium husks are mixed with an aqueous solution of the water soluble, low viscosity gum, preferably by fluid bed agglomeration, and dried. The composition is employed to treat constipation by ingesting an effective amount of the dietary fiber combinate dispersed in water. The use of the naturally occurring soluble fiber in the form of the gum acacia water solution will effect optimal dispersion of agglomerated psyllium hydrophilic mucilloid powder optionally containing a high intensity sweetener and any of a variety of combinate materials.

DESCRIPTION OF THE PREFERRED EMBODIMENTS

The psyllium hydrophilic mucilloid powder employed in the preferred embodiment of the invention has been found to be effectively dispersed as a high fiber composition, or in a laxative composition, by combination with a water soluble, low viscosity gum. The gum is preferably prepared in an aqueous solution, combined with the psyllium husk powder and dried to form a powdered, free flowing agglomerate. Water solubility of the gum should preferably be at least about 5% and may range up to 50% or more (by volume), while maintaining viscosity below about 1000 centipoises (cps). Gum acacia (also known as gum arabic or kordofan gum) is a natural sap exudate produced by various species of the acacia tree grown throughout the gum belt of Africa, and is the preferred high solubility, low viscosity gum employed. Gum acacia has properties which are fairly unique among the natural gums because of its high water solubility and unusual ability to dissolve, suspend, or emulsify other materials. Most natural gums cannot be dissolved in water at concentrations higher than 2-5% because of their very high viscosities. It has been found that gum acacia on the other hand can yield solutions of up to 55% concentration. For example, a 25% by volume solution of gum acacia will have a viscosity of 70-150 cps. By contrast, a 1% water solution of guar gum will have a viscosity of from about 2600 to about 5000 cps and a 1% solution of locust bean gum will have viscosity of from about 2000 cps to about 3000 cps. Gum acacia is especially useful where a gear type pump is employed in processing, such as in a Freund type spray agglomerator, where the limiting solution viscosity is about 1000 cps.

Gum acacia is considered to be generally recognized as safe by the U.S. Food and Drug Administration and is an official United States Pharmacopeia ("USP") listed material. Gum acacia is additionally nutritionally characterized as a soluble fiber. Aqueous solutions of gum acacia are acid to litmus. The equivalent of 0.002–0.011 g of potassium hydroxide may be necessary to completely neutralize one gram of gum acacia. Additionally, dilute mineral acids hydrolyze gum acacia to arabinose, galactose, aldobionic, and galacturonic acids.

The inclusion of a sweetening agent, necessary to impart a satisfactory sweet taste to the finished product when suspended in water, is preferably limited in this invention to low calorie, high intensity, non-sugar sweetening agents which add sweetness without adding bulk, such as aspartame, saccharine salts, cyclamate salts, acesulphame salts, steviosides, and other dipeptide sweeteners. Blends of any of these or other low calorie, high intensity sweeteners are also useful. In the further practice of the invention maltol and ethyl maltol are used to further build the sweetness of the high intensity sweeteners and to augment the flavor system. The sweetening agent is preferably added to the psyllium hydrophilic mucilloid powder before or during agglomeration with the aqueous gum solution. Flavoring agents such as volatile oils or other pharmacologically acceptable natural or synthetic agents, as well as vitamins and other oleagenous nutritional additives may be incorporated with the psyllium hydrophilic mucilloid powder in the same manner. Examples of flavoring agents include natural raspberry flavor, and examples of nutritional additives include beta carotene and vitamin E, particularly dl- or d-alpha-tocopherol (including the acetate form). Additionally, one or more excipients such as a polyhydric alcohol, preferably mannitol in powdered form, may be added to the psyllium hydrophilic mucilloid powder before or during agglomeration to aid in dispersion in the fluid bed agglomerator.

The final agglomerate of the present invention may also include a therapeutically active transit motility enhancer such as concentrated sennoside containing senna leaf extract. Dried senna leaf extract concentrates of commerce are listed in the USP, and such extract concentrate is recognized as an effective, efficient, and gentle laxative. The dried senna leaf extract concentrate is comprised mainly of sennosides A and B and its method of analysis is detailed in USP XVII. Such extract concentrate is preferably added to produce the agglomerated combinate of psyllium hydrophilic mucilloid by first combining and mixing it with the aqueous solution of the high solubility, low viscosity gum, preferably gum acacia. Optionally, a food grade ethoxylated surfactant such as polyoxyl 40 stearate, may be added at the same time.

The preferred method of manufacture for the generation of the psyllium hydrophilic mucilloid combinates of this invention then proceeds by spray agglomeration, although conventional, well known granulation or agglomeration techniques may be utilized. Drying of the agglomerated material is by standard drying techniques, such as conventional hot air drying means or, more preferably, by fluid bed drying. Since the gum acacia is a soluble fiber, the quantity of gum acacia used in the practice of this invention is not critical. The preferred quantity of acacia used to form the agglomerate, however, is in the range of about 0.5 to about 20.0% of the total dry combinate product weight, more preferably in the range of about 1.0–5.0%, and most preferably in the range of about 2.5–3.0%. The concentration of the aqueous solution of gum acacia may vary, and is preferably in the range of from about 8.0 to about 25.0% by volume.

In the practice of the current invention, the gum acacia readily solubilizes and/or suspends the sennoside concentrates so that there is little or no difficulty in delivering the sennosides through the pump system to the agglomeration bed and achieving excellent and ultimate distribution throughout the base containing psyllium hydrophilic mucilloid and any high intensity sweetener, flavor, or nutritional additive such as beta carotene.

Fluidized bed agglomeration, more commonly referred to as spray granulation, is faster than conventional two step granulations, can be accomplished within a single processing unit, and additionally allows for the elimination of cross contamination and adherence to good manufacturing practices. Fluidized bed spray agglomeration facilitates ultimate distribution of particles on or in an agglomeration bed. The liquid used to agglomerate a fluidized bed is introduced as a finely dispersed air atomized droplet or fog. Spray agglomeration of a fluidized bed with a solution containing a binder and an active ingredient is believed to represent the best agglomeration method for effecting ultimate distribution of both the binder and the active component.

During the spray granulation process, the bed to be agglomerated is kept in motion by filtered, heated, high velocity air. While the bed is in motion, an air-atomized agglomeration solution or suspension, with or without a therapeutically active component, is intermittently sprayed onto the dynamic fluidized bed. Following each spray cycle the bed containment filters are purged in order to return any unagglomerated material to the bed. The bed is again fluidized and the spray-filter purge cycles are continued until the entire dynamic fluidized bed has been uniformly agglomerated and the spray agglomeration solution or suspension has been exhausted. The final particle size of substantially all of the agglomerated combinate (combined particle) of the present invention is preferably greater than about 80 mesh (177 microns). The completed dry granulated agglomerate of the present invention may comprise from about 2–20% by weight gum acacia, balance psyllium hydrophilic mucilloid powder and, optionally, other added components. The psyllium hydrophilic mucilloid powder preferably comprises a major amount of the dry agglomerate and is more preferably present in an amount of about 80–98% by weight of the total dry agglomerate.

The process of agglomeration as practiced in the present invention effects the generation of dust free, low density, highly porous particles that are characteristically and generally spherical in shape. The dust free, low density, highly porous, generally spherical agglomerates of this invention demonstrate unusually good flow properties and facilitate high speed, dust free machine filling into any container. The granulated combinate of dry, free-flowing, agglomerated psyllium hydrophilic mucilloid powder, gum acacia and any optional ingredients may be administered to the gastro-intestinal tract in unit dose form of a desired effective amount (usually about 3.5 g for the average person) by adding it to water and stirring to achieve a rapid and smooth dispersion, and then by drinking it. The use of the gum ensures that the dosage administered maintains a high fiber content while effecting improved dispersion in water, without generating immediate high viscosity which interferes with drinking.

Among the preferred compositions which may be prepared in accordance with the present invention are the following:

1. A bulk fiber composition comprising psyllium powder agglomerated with gum acacia (as described previously), preferably containing a surfactant such as polyoxyl 40 stearate, a high intensity sweetener, and a flavor, in the following approximate preferred amounts (by weight percentage of final dry composition):

| psyllium husk powder | 90–97% |
|---|---|
| gum acacia | 2.5–5.0% |
| sweetener | 0.4–0.6% |
| flavorant | 0.5–2.5% |
| surfactant | 0.05–0.09% |

2. A bulk fiber composition comprising psyllium powder and a nutritional additive, such as beta carotene, agglomerated with gum acacia (as described previously), preferably containing a surfactant such as polyoxyl 40 stearate, a high intensity sweetener, and a flavor, in the following approximate preferred amounts (by weight percentage of final dry composition):

| psyllium husk powder | 90–97% |
|---|---|
| gum acacia | 2.5–5.0% |
| sweetener | 0.4–0.6% |
| flavorant | 0.5–2.5% |
| surfactant | 0.05–0.09% |
| nutritional additive | 0.00010–0.001% |

3. A bulk fiber composition for use as a laxitive comprising psyllium powder and USP sennosides agglomerated with gum acacia (as described previously), preferably containing a surfactant such as polyoxyl 40 stearate, a high intensity sweetener, and a flavor, in the following approximate preferred amounts (by weight percentage of final dry composition):

| psyllium husk powder | 90–97% | |
|---|---|---|
| gum acacia | 2.5–5.0% | |
| sweetener | 0.4–0.6% | |
| flavorant | 0.5–2.5% | |
| surfactant | 0.05–0.09% | |
| sennosides | 0.43–0.86% | (more pref. 0.57%) |

4. A general use bulk fiber composition of psyllium husk powder agglomerated with gum acacia, in which psyllium represents the major fiber source in an amount of at least about 40 weight percent, more preferably at least about 60 weight percent of the final dry composition.

5. A general use bulk fiber composition of psyllium husk powder agglomerated with gum acacia, and further including an excipient such as a polyhydric alcohol (preferably mannitol) in which the excipient represents up to about 40–60 weight percent of the final dry composition.

EXAMPLES

The following examples will serve to further illustrate the components and details of preparation for the psyllium hydrophilic mucilloid combinates of this invention. The invention, which is set forth in the foregoing disclosure, is not to be construed as being limited either in spirit or scope by these examples but rather by the claims set forth. Additionally, it should be recognized that those skilled in the art will readily realize that known variations and conditions and processes of the following preparations exist.

Example No. 1

A bench model mini flo-coater fluid bed agglomerator product bowl was charged with:

| Psyllium Husk Powder | 403.0 g |
|---|---|
| Aspartame | 1.6 g |

The bed was fluidized and mixed for a period of 5 minutes.

An agglomerating pump solution was prepared as follows:

| Acacia Powder | 10.0 g |
|---|---|
| Water | 110.0 ml |

The acacia water solution was heated up 35° C. and stirred until clear.

The bed was energized with inlet air temperature at 70° C. and the pump solution was delivered at a rate of 5 ml/minute with atomizing air pressure of 0.5 ATM.

The pump solution was delivered intermittently in 1 minute cycles, followed by air purging of the filter, and the cycles were continued until all of the acacia solution was delivered. The product was then dried to a loss on drying (LOD) moisture content of 8.5%.

The finished dust free product dispersed in water with no surface particles in evidence after 30 seconds with gentle stirring. The suspended product had a sweet non psyllium taste and contained 3.4 g of total dietary fiber per 3.5 g dose.

Example No. 2

A bench model mini-flo coater fluid bed agglomerator product bowl was charged with:

| | |
|---|---|
| Psyllium Husk Powder | 403.0 g |
| Aspartame | 1.6 g |

The bed was fluidized and mixed for a period of 5 minutes.

An agglomerating pump solution was prepared as follows:

| | |
|---|---|
| Acacia Powder | 10.0 g |
| MYRJ 52 (Polyoxyethylene 40 Stearate or Poloxyl 40 Stearate N.F.) | 0.4 g |
| Water | 110.0 ml |

The acacia, surfactant water solution was heated to 37° C. and stirred until clear.

The bed was energized and agglomerated as in Example No. 1.

The finished dust free product demonstrated rapid and smooth dispersion in water with no surface particles in evidence. The suspended product had a pleasant non psyllium taste and contained 3.48 g of total dietary fiber per 3.5 g dose.

Example No. 3

A bench model mini flo-coater fluid bed agglomerator product bowl was charged with:

| | |
|---|---|
| Psyllium Husk Powder | 404.2 g |
| Aspartame | 1.7 g |
| Seedless Freeze Dried Raspberry Powder | 8.5 g |

The bed was fluidized and mixed for a period of 5 minutes.

An agglomerating pump solution was prepared as follows:

| | |
|---|---|
| Acacia Powder | 10.0 g |
| Polyoxyl 40 Stearate N.F. | 0.4 g |
| Water | 110.0 ml |

The acacia surfactant solution was heated to 37° C. and stirred until clear. The system was then energized and agglomerated as in Example No. 1.

The finished dust free product demonstrated rapid and smooth dispersion in water with no surface particles evident. The suspended product had a pleasant non psyllium taste and a total dietary fiber content of 3.48 g per 3.5 g dose.

Example No. 4

A bench model mini flo-coater fluid bed agglomerator was charged with:

| | |
|---|---|
| Pysllium Husk Powder | 437.31 g |
| Aspartame | 1.80 g |
| Beta Carotene Adsorbate (Valentine Enterprises, Inc. or VEI) | 0.64 g |
| Natural Raspberry Flavor (Takasago) | 9.00 g |

The bed was energized to effect fluidization and mixed for 5 minutes.

An agglomerating pump solution was prepared as follows:

| | |
|---|---|
| Acacia Powder | 11.25 g |
| Polyoxyl 40 Stearate N.F. | 0.40 g |
| Water | 125.00 ml |

The acacia surfactant water solution was heated to 37° C. and stirred until clear. The bed was energized and agglomerated as in Example No. 1.

The finished dust free product demonstrated rapid and smooth dispersion in water with no surface particles in evidence. The suspended product had a pleasant non psyllium taste, a beta carotene content equivalent to 1,000 IU of vitamin A, and a total dietary content of 3.4 g per 3.5 g dose.

Example No. 5

Example No. 4 was repeated with the following changes in the pump agglomerating solution: polysorbate 20 NF was substituted for the polyoxyl 40 stearate.

The finished dust free product demonstrated rapid and smooth dispersion in water with no surface particles in evidence. The suspended product had a pleasant non psyllium taste, a beta carotene content equivalent to 1,000 IU of vitamin A and a total dietary fiber content of 3.4 g per 3.5 g dose.

Example No. 6

Example No. 4 was repeated with the following changes in the pump agglomerating solution: polysorbate 80 was substituted for the polyoxyl 40 stearate.

The finished dust free product demonstrated rapid and smooth dispersion in water with no surface particles in evidence. The suspended product had a pleasant non psyllium taste, a beta carotene content equivalent to 1,000 IU of vitamin A and a total dietary fiber content of 3.4 g per 3.5 g dose.

Example No. 7

A bench model mini flo-coater fluid bed agglomerator product bowl was charged with:

| | |
|---|---|
| Psyllium Husk Powder | 427.29 g |
| Aspartame | 1.80 g |
| Seedless Freeze Dried Raspberry Powder | 4.50 g |
| Natural Raspberry Flavor | 4.50 g |

The bed was energized to effect fluidization and mixed for a period of 5 minutes.

An agglomerating pump emulsion was prepared as follows:

| | |
|---|---|
| Acacia Powder | 11.25 g |
| Polyoxy 40 Stearate N.F. | 0.40 g |
| 30% Beta Carotene in Oil | 0.26 g |
| Water | 110.00 ml |

The acacia surfactant solution was heated to 60° C. and stirred until clear. The beta carotene in oil was added and an oil in water emulsion was formed with the aid of high shear stirring and a piston pump homogenizer.

The bed was energized and agglomerated as in Example No. 1.

The finished dust free agglomerated product demonstrated rapid and smooth dispersion in water with no surface particles in evidence. The suspended product had a pleasant non psyllium taste and contained beta carotene equivalent to 1,000 IU of vitamin A and a total dietary fiber content of 3.4 g per 3.5 g dose.

Example No. 8

A bench model mini flo-coater fluid bed agglomerator product bowl was charged with:

| | |
|---|---|
| Psyllium Husk Powder | 426.01 g |
| Aspartame | 1.08 g |
| Acesulphame | 0.72 g |
| Seedless Freeze Dried Raspberry Powder | 9.00 g |

The bed was energized to effect fluidization and mixed for a period of 5 minutes.

An agglomerating pump emulsion was prepared as follows:

| | |
|---|---|
| Acacia Powder | 11.25 g |
| Polyoxyl 40 Stearate | 0.40 g |
| 30% Beta Carotene in oil | 0.26 g |
| d Alpha Tocopherol | 1.28 g |
| Water | 110.00 ml |

The acacia surfactant solution was heated to 60° C. and stirred until clear. The beta carotene in oil and the natural vitamin E oil were added and an oil in water emulsion was formed with the aid of high shear stirring and a piston pump homogenizer.

The bed was energized and agglomerated as in Example No. 1. The finished dust free product demonstrated rapid and smooth dispersion in water with no surface particles in evidence. The suspended product had a pleasant non psyllium taste, a beta carotene content equivalent to 1,000 IU of vitamin A, vitamin E content of 10 IU and total dietary fiber content of 3.4 g per 3.5 g dose.

Example No. 9

A bench model mini flo-coater fluid bed agglomerator product bowl was charged with:

| | |
|---|---|
| Psyllium Husk Powder | 424.01 g |
| Aspartame | 1.08 g |
| Acesulphame | 0.72 g |
| Natural Raspberry Flavor | 9.00 g |
| Beta Carotene Adsorbate (VEI) | 0.64 g |
| d Alpha Tocopherol | 3.20 g |
| Adsorbate (VEI) | |

The bed was energized to effect fluidization and mixed for a period of 5 minutes.

An agglomerating pump solution was prepared as follows:

| | |
|---|---|
| Acacia Powder | 11.25 g |
| Polyoxyl 40 Stearate | 0.40 g |
| Water | 110.00 ml |

The acacia surfactant solution was heated to 60° C. and stirred until clear. The bed was energized and agglomerated as in Example No. 1.

The finished dust free product demonstrated rapid and smooth dispersion in water with no surface particles in evidence. The suspended product had a pleasant non psyllium taste, a beta carotene content equivalent to 1,000 IU of vitamin A, Vitamin E content of 10 IU, and a total dietary fiber content of 3.4 g per 3.5 g dose.

Example No. 10

A bench model mini flo-coater fluid bed agglomerator product bowl was charged with:

| | |
|---|---|
| Psyllium Husk Powder | 425.35 g |
| Aspartame | 1.80 g |
| Seedless Freeze Dried Raspberry Powder | 9.00 g |

The bed was energized to effect fluidization and mixed for a period of 5 minutes.

An agglomerating pump solution was prepared as follows:

| | |
|---|---|
| Acacia Powder | 11.25 g |
| Sennoside Powder USP (100% Sennosides) | 2.60 g |
| Water | 115.00 ml |

The acacia sennoside solution was heated to 40° C. and stirred until clear and uniform. The bed was energized and agglomerated as in Example No. 1.

The finished dust free product demonstrated rapid and smooth dispersion in water with no surface particles in evidence. The suspended product had a pleasant non psyllium taste and contained 20 mg of Sennosides A & B and total dietary fiber content of 3.43 g per 3.5 g dose.

Example No. 11

A bench model mini flo-coater fluid bed agglomerator product bowl was charged with:

| | |
|---|---|
| Psyllium Husk Powder | 424.9 g |
| Aspartame | 1.0 g |
| Acesulphame | 0.8 g |
| Seedless Freeze Dried Raspberry Powder | 4.5 g |
| Natural Raspberry Flavor Powder | 4.50 g |

The bed was energized to effect fluidization and mixed for a period of 5 minutes.

An agglomeration pump solution was prepared as follows:

| | |
|---|---|
| Acacia Powder | 11.3 g |
| Polyoxyl 40 Stearate N.F. | 0.4 g |
| Sennoside Powder USP (100% Sennosides) | 2.6 g |
| Water | 115.0 ml |

The acacia, surfactant and sennoside solution was heated to 40° C. and stirred until clear and uniform. The bed was energized and agglomerated as in Example No. 1.

The finished dust free product demonstrated rapid and smooth dispersion in water with no surface particles in evidence. The suspended product had a pleasant non psyllium taste and contained 20 mg of Sennosides A & B with a total dietary fiber content of 3.4 g per 3.5 g dose.

Example No. 12

A bench model mini flo-coater fluid bed agglomerator product bowl was charged with:

| | |
|---|---|
| Psyllium Husk Powder | 424.31 g |
| Aspartame | 1.00 g |
| Acesulphame | 0.70 g |
| Maltol (Veltol, Pfizer) | 0.10 g |
| Beta Carotene Adsorbate (VEI) | 0.64 g |
| Natural Raspberry Flavor | 9.00 g | the bed was energized to effect fluidization and mixed for a period of 5 minutes.

An agglomerating pump solution was prepared as follows:

| | |
|---|---|
| Acacia Powder | 11.25 g |
| Sennoside Powder USP (100% Sennosides) | 2.60 g |
| Polyol 40 Stearate N.F. | 0.40 g |
| Water | 125.00 ml |

The acacia surfactant, and sennoside pump solution was heated to 40° C. and stirred until clear. The bed was energized and agglomerated as in Example No. 1.

The finished dust free product demonstrated rapid and smooth dispersion water with no surface particles in evidence. The suspended product had a pleasant non-psyllium taste, a beta carotene content equivalent to 1,000 IU of vitamin A, and sennoside content of 20 mg Sennosides A & B and a total dietary fiber content of 3.4 g per 3.5 g dose.

Example 13

A bench model mini flo-coater fluid bed agglomerator product bowl was charged with:

| | |
|---|---|
| Psyllium Husk Powder | 424.69 g |
| Aspartame | 1.00 g |
| Acesulphame | 0.70 g |
| Maltol (Velto, Pfizer) | 0.10 g |
| Natural Raspberry Flavor | 9.00 g |

The bed was energized to effect fluidization and mixed for a period of 5 minutes.

An agglomerating pump emulsion was prepared as follows:

| | |
|---|---|
| Acacia Powder | 11.25 g |
| Sennoside Powder USP (100% Sennosides) | 2.60 g |
| Polyoxyl 40 Stearate N.F. | 0.40 g |
| 30% Beta Carotene in Oil | 0.26 g |
| Water | 125.00 ml |

The acacia surfactant and sennoside solution was heated to 60° C. and stirred until clear. The beta carotene in oil was added and an oil in water emulsion was formed with the aid of high shear stirring and a piston pump homogenizer.

The bed was energized and agglomerated as in Example No. 1. The finished dust free agglomerated product demonstrated rapid and smooth dispersion in water with no surface particles in evidence. The suspended product had a pleasant non psyllium taste and contained beta carotene equivalent to 1,000 IU of vitamin A, 20 mg of Sennosides A & B, and a total dietary fiber content of 3.4 g per 3.5 g dose.

Example No. 14

A bench model mini flo-coater fluid bed agglomerator product bowl was charged with:

| | |
|---|---|
| Psyllium Husk Powder | 424.31 g |
| Aspartame | 0.90 g |
| Acesulphame | 0.70 g |
| Sodium Saccharine | 0.10 g |
| Maltol (Veltol, Pfizer) | 0.10 g |
| Beta Carotene Adsorbate (VEI) | 0.64 g |
| Natural Raspberry Flavor | 9.00 g |

The bed was energized to effect fluidization and mixed for a period of 5 minutes.

An agglomerating pump solution was prepared as follows:

| | |
|---|---|
| Acacia Powder | 11.25 g |
| Sennoside Powder USP (100% Sennosides) | 2.60 g |
| Polysorbate 80 N.F. | 0.40 g |
| Water | 125.00 ml |

The acacia surfactant sennoside pump solution was heated to 40° C. and stirred until clear. The bed was energized and agglomerated as in Example No. 1.

The finished dust free product demonstrated rapid and smooth dispersion in water with no surface particles in evidence. The suspended product had a pleasant non psyllium taste, a beta carotene content equivalent to 1,000 IU of vitamin in A, a sennoside content of 20 mg Sennosides A & B and a total dietary fiber content of 3.4 g per 3.5 g dose.

Example No. 15

A bench model mini flo-coater fluid bed agglomerator product bowl was charged with:

| | |
|---|---|
| Pysllium Husk Powder | 424.31 g |
| Aspartame | 0.90 g |
| Acesulphame | 0.70 g |
| Maltol (Veltol, Pfizer) | 0.10 g |
| Calcium Cyclamate | 0.10 g |
| Beta Carotene Adsorbate | 0.64 g |
| Seedless Freeze Dried | 9.00 g |

| -continued |
|---|
| Raspberry Powder |

The bed was energized to effect fluidization and mixed for a period of 5 minutes.

An agglomeration pump solution was prepared as follows:

| Acacia Powder | 11.25 g |
|---|---|
| Sennoside Powder USP (100% Sennosides) | 2.60 g |
| Polysorbate 20 N.F. | 0.40 g |
| Water | 125.00 ml |

The acacia surfactant, sennoside pump solution was heated to 40° C. and stirred until clear. The bed was energized and agglomerated as in Example No. 1.

The finished dust free product demonstrated rapid and smooth dispersion in water with no surface particles in evidence. The suspended product had a pleasant non psyllium taste, a beta carotene content equivalent to 1,000 IU of vitamin A, a sennoside content of 20 mg Sennosides A & B and a total dietary content of 3.4 g per 3.5 g dose.

Example No. 16

A bench model mini flo-coater fluid bed agglomerator product bowl was charged with:

| Psyllium Husk Powder | 225.97 g |
|---|---|
| Mannitol Powder | 200.00 g |
| Raspberry Powder | 9.00 g |
| Aspartame | 1.80 g |

The bed was energized to effect fluidization and mixed for a period of 5 minutes.

An agglomerating pump solution was prepared as follows:

| Acacia Powder | 11.25 g |
|---|---|
| Sennoside Powder USP (100% Sennosides) | 1.53 g |
| Water | 125.00 ml |

The acacia surfactant sennoside solution was heated to 60° C. and stirred until clear.

The bed was energized and agglomerated as in Example No. 1.

The finished dust free agglomerated product demonstrated rapid and smooth dispersion in water with no surface particles in evidence. The suspended product had a pleasant non psyllium taste and contained 20 mg Sennosides A & B, 2.7 g, Mannitol and a total dietary fiber content of 3.25 g per 6.0 g dose.

Example No. 17

A bench model mini flo-coater fluid bed agglomerator product bowl was charged with:

| Psyllium Husk Powder | 226.0 g |
|---|---|
| Oat Bran Powder | 51.5 g |
| Pectin Powder | 50.0 g |
| Rice Bran Powder | 50.0 g |
| Barley Bran Powder | 50.0 g |
| Raspberry Powder | 9.0 g |

| -continued |
|---|
| Aspartame | 1.8 g |

The bed was energized to effect fluidization and mixed for a period of 5 minutes.

An agglomerating pump solution was prepared as follows:

| Acacia Powder | 11.25 g |
|---|---|
| Polyoxyl 40 Stearate | 0.45 |
| Water | 125.00 ml |

The acacia surfactant water solution was heated to 37° C. and stirred until clear. The bed was energized and agglomerated as in Example No. 1.

The finished dust free product demonstrated rapid and smooth dispersion in water with no surface particles in evidence. The suspended product had a pleasant taste and a total dietary fiber content of 3.46 g per 3.5 g dose.

Example No. 18

A 140 liter product bowl of a Freund flo-coater model FL-80 was charged with:

| Psyllium Husk Powder | 47.433 kg |
|---|---|
| Aspartame N.F. | 0.200 kg |
| Beta Carotene Adsorbate (VEI 12% Beta Carotene) | 0.072 kg |
| Natural Raspberry Flavor | 1.000 kg |

The aspartame (0.2 kg) was mixed with 5 kg of the psyllium husk power and milled through a comill to assure adequate distribution of the aspartame before charging into the product bowl.

An agglomerating pump solution was prepared as follows:

| Acacia Powder N.F. | 1.250 kg |
|---|---|
| Polyoxyl 40 Stearate | 0.045 kg |
| Water for Solution | [10.000 l]* |
| Water for System Flush | [2.000 l]* |

*Removed during processing 10 liters of water were charged into a mixing tank and heated to 85° C. with stirring; the polyoxyl 40 stearate was added to the water and then the acacia powder (1.25 kg) was added slowly and agitation continued until the agglomerating solution was clear.

The product bowl containing the materials to be agglomerated was positioned in the machine and lifted into place to seal the chamber.

The following operational parameters for the agglomeration run were set prior to the energizing of the machine.

| Inlet Air | 70° C. |
|---|---|
| Air Pressure to Guns | 2.5 Atmospheres |
| ATM Pump Delivery Rate | 0.6 L/Min |
| Pump Cycle | 1.5 Min |
| Mechanical Filter Shake | 12 Seconds |
| Number of Pump/Shake Cycles | 14 |
| Atomizing Air to Spray Guns | 170 L/Hr. |
| Pattern Air to Spray Guns | 20 L/Hr |
| Bed Mix Time | 5.0 Min |

With the established parameters entered into the electronic control system of the FL-80 the machine was energized and fluidization of the bed was effected.

After each minute of time in the mix cycle fluidization was interrupted and the filters were automatically shaken followed by reestablished fluidization. Following the mix cycle atomized agglomerating pump solution was delivered onto the bed for 1.5 minutes. Fluidization of the bed was interrupted and followed by filter shaking to return unagglomerated material to be bed. The spray/shake cycles continued until all of the pump atomizing solution plus the system flush water was delivered to the bed.

The bed was then dried by fluidization in the 70° C. inlet air with the same intermittent shaking cycle interval as in the mixing mode. The final product was removed at a moisture content of 8.8% LOD determined via computrac moisture analysis.

The finished, dust free, agglomerated product demonstrated rapid and smooth dispersion in water with no surface particles in evidence. The suspended product had a non psyllium pleasant taste and contained beta carotene equivalent to 1,000 IU of vitamin A and a total dietary fiber content of 3.4 g per 3.5 g dose.

Example No. 19

A 140 liter product bowl of a Freund model FL-80 flo-coater was charged with:

| Psyllium Husk Powder | 47.220 kg |
| Aspartame N.F. | 0.200 kg |
| Natural Raspberry Flavor | 1.000 kg |

The aspartame N.F. 0.2 kg was mixed with 5 kg of the psyllium husk powder and milled through a comill to assure adequate distribution of the aspartame before charging into the product bowl.

An agglomerating pump solution was prepared as follows:

| Acacia Powder N.F. | 1.250 kg |
| Poloxyl 40 Stearate | 0.045 kg |
| Sennoside Powder USP (100% Sennosides) | 0.285 kg |
| Water for solution | [10.000 l]* |
| Water for System Flush | [2.000 l]* |

*Removed During Processing 10 liters of water were charged into a mixing tank and heated to 85° C. with stirring; the polyoxyl 40 stearate and the sennoside powder were added to the water and then the acacia was slowly added to the water and agitation continued until the agglomerating solution was clear.

The product bowl containing the materials to be agglomerated was positioned in the machine and lifted into place to seal the unit.

The operational parameters and machine functionality were the same as employed in Example No. 16. The finished dust free agglomerated product demonstrated rapid and smooth dispersion in water with no surface particles in evidence. The suspended product had a non psyllium pleasant taste and contained 20 mg of sennosides, Sennosides A & B, beta carotene equivalent to 1,000 IU of vitamin A and a total dietary fiber content of 3.4 g per 3.5 g dose.

Example No. 20

A 140 liter product bowl of a Freund model FL-80 flo-coater was charged with:

| Psyllium Husk Powder | 47.505 kg |
| Aspartame N.F. | 0.200 kg |
| Natural Raspberry Flavor | 1.000 kg |

The aspartame N.F. 0.2 kg was mixed with 5 kg of the psyllium husk powder and milled through a comill to assure adequate distribution of the aspartame before charging into the product bowl.

An agglomerating pump solution was prepared as follows:

| Acacia Powder N.F. | 1.250 kg |
| Poloxyl 40 Stearate | 0.045 kg |
| Water for solution | [10.000 l]* |
| Water for System Flush | [2.000 l]* |

*Removed During Processing 10 liters of water were charged into a mixing tank and heated to 85° C. with stirring; the polyoxyl 40 stearate and the sennoside powder were added to the water and then the acacia was slowly added to the water and agitation continued until the agglomerating solution was clear.

The product bowl containing the materials to be agglomerated was positioned in the machine and lifted into place to seal the unit.

The operational parameters and machine functionality were the same as employed in Example No. 16. The finished dust free agglomerated product demonstrated rapid and smooth dispersion in water with no surface particles in evidence. The suspended product had a non psyllium pleasant taste and contained a total dietary fiber content of 3.4 g per 3.5 g dose.

While the invention has been described with reference to specific embodiments, it will be recognized by those skilled in the art that variations are possible without departing from the spirit and scope of the invention, and that it is intended to cover all such changes and modifications of the invention disclosed herein fro the purpose of illustration which do not constitute departure from the spirit and scope of the invention.

Thus, having described the invention,

What is claimed is:

1. A process for producing a bulk fiber composition containing a therapeutically active ingredient consisting essentially of:
   a) preparing an aqueous solution of a water soluble, low viscosity gum and adding thereto a therapeutically active ingredient;
   b) mixing powdered psyllium husks with said aqueous solution of a water soluble, low viscosity gum, containing said active ingredient by fluidized bed agglomeration; and
   c) drying the mixture to form a dry, free-flowing, water dispersible, agglomerated dietary fiber combinate.

2. The process of claim 1 wherein said water soluble, low viscosity gum comprises gum acacia.

3. The process of claim 1 wherein said water soluble, low viscosity gum comprises gum acacia in an amount of about 0.5–20% by weight of the dry combinate.

4. The process of claim 3 wherein said powdered psyllium husks are present in an amount of from about 40-98% by weight of the dry combinate.

5. The process of claim 1 wherein food grade ethoxylated surfactants are added to the gum solution prior to mixing with the psyllium husk powder.

6. The process of claim 1 wherein polyhydric alcohol is added to said psyllium husk powder.

7. The process of claim 1 wherein concentrated, sennoside containing senna leaf extract is added as a laxating agent to the gum solution prior to mixing with the psyllium husk powder.

8. The process of claim 1 wherein one or more of a low calorie, high intensity, non sugar sweetener or nutritional oleagenous ingredient is added to said psyllium husk powder.

9. A consumable bulk fiber composition consisting essentially of powdered psyllium husks agglomerated with gum acacia, said powdered psyllium husks being present in an amount of at least about 40 percent by weight and said gum acacia being present in an amount of at least about 2.5 percent by weight of said composition, to form a dry, free-flowing, water dispersible dietary fiber combinate.

10. The composition of claim 9 wherein said powdered psyllium husks are present in an amount of at least about 80 percent by weight of said composition.

11. A consumable bulk fiber composition consisting essentially of powdered psyllium husks agglomerated with gum acacia, and a food grade ethoxylated surfactant, said powdered psyllium husks being present in an amount of at least about 40 percent by weight and said gum acacia being present in an amount of at least about 2.5 percent by weight of said composition, to form a dry, free-flowing, water dispersible dietary fiber combinate.

12. A consumable bulk fiber composition consisting essentially of powdered psyllium husks agglomerated with gum acacia, and an excipient, said powdered psyllium husks being present in an amount of at least about 40 percent by weight, said gum acacia being present in an amount of at least about 2.5 percent by weight of said composition and said excipient being present in an amount of at least 40 percent by weight of said composition, to form a dry, free-flowing, water dispersible dietary fiber combinate.

13. A consumable bulk fiber composition consisting essentially of powdered psyllium husks agglomerated with gum acacia, and a polyhydric alcohol, said powdered psyllium husks being present in an amount of at least about 40 percent by weight and said gum acacia being present in an amount of at least about 2.5 percent by weight of said composition, to form a dry, free-flowing, water dispersible dietary fiber combinate.

14. A consumable bulk fiber composition consisting essentially of powdered psyllium husks agglomerated with gum acacia, and a concentrated sennoside containing senna leaf extract, said powdered psyllium husks being present in an amount of at least about 40 percent by weight and said gum acacia being present in an amount of at least about 2.5 percent by weight of said composition, to form a dry, free-flowing, water dispersible dietary fiber combinate.

15. A consumable bulk fiber composition consisting essentially of powdered psyllium husks agglomerated with gum acacia, and a low calorie, high intensity, non sugar sweetener, said powdered psyllium husks being present in an amount of at least about 40 percent by weight and said gum acacia being present in an amount of at least about 2.5 percent by weight of said composition, to form a dry, free-flowing, water dispersible dietary fiber combinate.

16. A consumable bulk fiber composition consisting essentially of powdered psyllium husks agglomerated with gum acacia, and a nutritional oleagenous ingredient, said powdered psyllium husks being present in an amount of at least about 40 percent by weight and said gum acacia being present in an amount of at least about 2.5 percent by weight of said composition, to form a dry, free-flowing, water dispersible dietary fiber combinate.

17. A consumable bulk fiber composition consisting essentially of powdered psyllium husks agglomerated with gum acacia, and beta carotene or dl-or d-alpha-tocopherol acetate, said powdered psyllium husks being present in an amount of at least about 40 percent by weight and said gum acacia being present in an amount of at least about 2.5 percent by weight of said composition, to form a dry, free-flowing, water dispersible dietary fiber combinate.

18. A process for producing a bulk fiber composition consisting essentially of:
   a) preparing an aqueous solution of gum acacia and, optionally, a therapeutically active ingredient;
   b) mixing powdered psyllium husks with said aqueous solution of gum acacia, said powdered psyllium husks being present in an amount to yield at least about 40 percent by weight of said composition after drying and said gum acacia being present in an amount to yield at least about 2.5 percent by weight of said composition after drying; and
   c) drying the mixture to form a dry, free-flowing, water dispersible, agglomerated dietary fiber combinate.

* * * * *